United States Patent [19]

Cimino

[11] Patent Number: 5,652,096

[45] Date of Patent: Jul. 29, 1997

[54] IDENTIFICATION OF ALLELE SPECIFIC NUCLEIC ACID SEQUENCES BY HYBRIDIZATION WITH CROSSLINKABLE OLIGONUCLEOTIDE PROBES

[75] Inventor: George D. Cimino, El Cerrito, Calif.

[73] Assignee: HRI Research Inc., Concord, Calif.

[21] Appl. No.: 231,440

[22] Filed: Apr. 20, 1994

Related U.S. Application Data

[63] Continuation of Ser. No. 850,244, Mar. 11, 1992, abandoned, which is a continuation of Ser. No. 225,725, Aug. 1, 1988, abandoned.

[51] Int. Cl.$^6$ ............................ C12Q 1/68; C07H 21/00
[52] U.S. Cl. ............................ 435/6; 435/91.1; 435/91.2; 435/803; 435/820; 436/501; 536/22.1; 536/25.3; 549/200; 549/218; 549/275; 935/77; 935/78
[58] Field of Search ............................ 435/6, 91.1, 91.2, 435/803, 820; 436/501; 536/22.1, 25.3; 549/200, 218, 275; 935/77, 78

[56] References Cited

U.S. PATENT DOCUMENTS

| | | | |
|---|---|---|---|
| 4,124,598 | 11/1978 | Hearst et al. | 260/347.21 |
| 4,169,204 | 9/1979 | Hearst et al. | 546/270 |
| 4,196,281 | 4/1980 | Hearst et al. | 536/28 |
| 4,559,303 | 12/1985 | Yabusaki et al. | 435/6 |
| 4,683,195 | 7/1987 | Mulllis et al. | 435/6 |
| 4,683,202 | 7/1987 | Mullis | 435/91 |

FOREIGN PATENT DOCUMENTS

| | | | |
|---|---|---|---|
| 0130523 | 9/1985 | European Pat. Off. | C12Q 1/68 |

OTHER PUBLICATIONS

Marmur and Lane, Proc. Nat. Acad. Sci., U.S.A. 46, 453 (1960).
Doty et al., Proc. Nat. Acad. Sci., U.S.A. 46, 461 (1960).
Hyashi et al., Proc. Nat. Acad. Sci., U.S.A. 50, 664 (1963).
Smith and Wilcox, J. Mol. Biol. 51, 379 (1970).
Southern, J. Mol. Biol. 98, 503 (1975).
Wallace et al., Biochimie 67, 755 (1985).
Studencki and Wallace, DNA 3, 7 (1984).
Studencki et al., Human Genetics 37, 42 (1985).
Wallace et al., Nucl. Acids Res. 6, 3543 (1979).
Wallace et al., Nucl. Acids Res. 879 (1981).
Saiki et al., Nature 324, 163 (1986).
Gamper et al., Photochem. Photobio. 40, 29 (1984).
Webb et al., Nuc. Acids Res. 14, 7661 (1986).
Heikkila et al., Acta Chem. Scand. B 37, 263 (1983).
Beaucage et al., Tetrahedron Letters 22, 1859 (1981).
Kremsky et al., Nucleic Acids Research 15, 2891 (1987).
Murakawa et al., DNA 7, 287 (1988).
Mullis, et al., Cold Springs Harbor Symposia, Cetus Corp., vol. LI, 263 (1986)
Caruthers, Science 230, 281 (1985).
Hearst, Journal Inv. Dermt. 77, 39 (1981).
Hearst, et al., Quarterly Rev. Biophysics 17, 1–44 (1984).
Tessman et al., Biochemistry 24, 1669 (1985).
Cimino et al., Ann. Rev. Biochem. 54, 1151 (1985).
Saiki, et al., Science, 230, 1350 (1985).
Johnston, et al., Science, 197, 906 (1977).
Gamper, et al., Nucl. Acid Res. 14, 9943 (1986).
Gamper, et al., J. Mol. Biol., 197, 349 (1987).
Lee et al., Biochemistry 27, 3197–3203 (1988).
Wood et al., Proc. Natl. Acad. Sci. 82, 1585–1588 (1985).
Jacobs et al., Nucleic Acids Res. 16, 4637–4650 (1988).
Meyers et al., Nature 313, 495–498 (1985).
Meyers, et al., Nucleic Acids Res. 13, 3111–3129 (1985).
Meyers et al., Nucleic Acids Res. 13, 3131–3145 (1985).
Tomic et al., Science 238, 1722–1725 (1987).
Ostrander et al., Nucleic Acids Research 16, 213 (1988).
Guiotto et al., Eur. J. Med. Chem. 16, 489 (1981).
Pieles et al., Nucleic Acids Research, 17, 285–299 (1989).
Teare et al., Nucleic Acids Research, 17, 3359–3372 (1989).
Sheffield et al., Proc. Natl. Acad. Sci. 86, 232–236 (1989).

*Primary Examiner*—W. Gary Jones
*Assistant Examiner*—Ardin H. Marschel
*Attorney, Agent, or Firm*—Medlen & Carroll

[57] ABSTRACT

Hybridization method for discriminating between complementarity and partial complementarity of DNA base sequences. Kinetic covalent entrapment of PCR-amplified target DNA is achieved through the use of crosslinkable probes. A crosslinking site is introduced into the target DNA via the PCR amplification process. Problems with renaturation of target DNA in the PCR process and in the hybridization reaction are minimized.

14 Claims, 12 Drawing Sheets

PCR PRODUCT OF NORMAL ($\beta^N$) GLOBIN = 135 bp; MW = 88,100

| | | |
|---|---|---|
| PCR PRIMERS | RIGHT PRIMER (C) | 3'-GTTCTGTCCAAATTCCTCTGGT-5' ⇨ KM-38 |
| | 5'-AC ACC ATG GTG CAC CTT ACT-3' LEFT PRIMER (W) | RS-118 |
| GENOMIC DNA SEQUENCE OF $\beta^N$ | 5'-AC ACC ATG GTG CAC CTG ACT CCT GAG GAG AAG TCT GCC GTT ACT GCC-3' | WATSON (W) |
| | 3'-TG TGG TAC CAC GTG GAC TGA GGA CTC CTC TTC AGA CGG CAA TGA CGG-5' | CRICK (C) |
| MONOADDUCTED PROBE | 5'- C CTT<sub>■</sub> ACT CCT GAG GAG -3' | HRI-04 |
| SYNTHETIC OLIGONUCLEO-TIDE TARGETS | 3'- G GAA TGA GGA CTC CTC TTC AGA CGG CAA TGA -5' | HRI-10 |
| | 3'- G GAA TGA GGA CAC CTC TTC AGA CGG CAA TGA -5' | HRI-11 |
| | 3'- G GAA TGA GGA TTC CTC TTC AGA CGG CAA TGA -5' | HRI-20 |

FIG. 1   HRI 04-MA SYSTEM

PCR PRODUCT OF NORMAL ($\beta^N$) GLOBIN = 174 bp; MW = 114,840

PCR PRIMERS:
⇐ 5'-GGTTGGCCAATCTACTCCCAGG-3'　　　　LEFT PRIMER (W)　　KM-29

3'-TC ATC AGA CGG CAA TGA CGG-5'　　RIGHT PRIMER (C)　　HRI-12

GENOMIC DNA SEQUENCE OF $\beta^N$:
5'-AC ACC ATG GTG CAC CTG ACT CCT GAG GAG AAG TCT GCC GTT ACT GCC-3'　WATSON (W)
3'-TG TGG TAC CAC GTG GAC TGA GGA CTC CTC TTC AGA CGG CAA TGA CGG-5'　CRICK (C)

MONO-ADDUCTED PROBES:
N-PROBE (W)　5'- CCT GAG GAG TAG TCT G -3'　　HRI-08 MA
S-PROBE (W)　5'- CCT GTG GAG TAG TCT G -3'　　HRI-19 MA

SYNTHETIC OLIGONUCLEOTIDE TARGETS:
3'- G GAC TGA GGA CTC CTC ATC AGA CGG CAA TGA -5'　HRI-16
3'- G GAC TGA GGA CAC CTC ATC AGA CGG CAA TGA -5'　HRI-17
3'- G GAC TGA GAA GGA CTT CTC ATC AGA CGG CAA TGA -5'　HRI-21
3'- G GAC TGA GGA CTC CTT ATC AGA CGG CAA TGA -5'　HRI-25
3'- G GAC TGA GGA CTC CAC ATC AGA CGG CAA TGA -5'　HRI-26

FIG. 2　　HRI 08-MA SYSTEM

| TYPE AND LOCATION OF SINGLE MISMATCH | TARGET OLIGO | PROBE OLIGO | HYBRID & IRRAD. TEMP. | FRACTION HYBRIDZD | DISCRIM-INATION |
|---|---|---|---|---|---|
| CONTROL | HRI 10 | 04-MA | 4°C | 0.252 | ---- |
| 5'-CCTT̲ACTCCTGAGGAG-3'  A↑ | HRI 11 | 04-MA | 4°C | 0.039 | 6.5 |
| CONTROL | HRI 10 | 04-MA | 27°C | 0.336 | ---- |
| A↑ | HRI 11 | 04-MA | 27°C | 0.026 | 12.9 |
| 04 PROBE 5'-CCTT̲ACTCCTGAGGAG-3' GENOMIC TARGET SEQUENCE 3'-GGACTGAGGAGGACTCCTCTTCAGACGGCAATGA-5' 08 PROBE 5'-CCTGAGGAGT̲AGTCTG-3' | | | | | |
| CONTROL | HRI 16 | 08-MA | 4°C | 0.677 | ---- |
| A↑ | HRI 17 | 08-MA | 4°C | 0.312 | 2.2 |
| T↑G | HRI 21 | 08-MA | 4°C | 0.243 | 2.8 |
| A↑A | HRI 26 | 08-MA | 4°C | 0.454 | 1.5 |
| T↑G | HRI 25 | 08-MA | 4°C | 0.661 | 1.0 |
| CONTROL | HRI 16 | 08-MA | 27°C | 0.620 | ---- |
| A↑ | HRI 17 | 08-MA | 27°C | 0.083 | 7.5 |
| T↑G | HRI 21 | 08-MA | 27°C | 0.087 | 7.1 |
| A↑A | HRI 26 | 08-MA | 27°C | 0.318 | 1.9 |
| T↑G | HRI 25 | 08-MA | 27°C | 0.468 | 1.3 |

FIG. 7

IDENTIFICATION OF ALLELE SPECIFIC NUCLEIC ACID SEQUENCES BY HYBRIDIZATION WITH CROSSLINKABLE OLIGONUCLEOTIDE PROBES

RELATED APPLICATION DATA

This application is a continuation of U.S. application Ser. No. 07/850,244, filed Mar. 11, 1992, now abandoned, which is a continuation of U.S. application Ser. No. 225,725, filed Aug. 1, 1988, now abandoned.

BACKGROUND OF THE INVENTION

1. Field of the Invention

The present invention relates to nucleic acid hybridization with crosslinkable oligonucleotide probes, and in particular, (1) a chemical synthesis route for the production of psoralen monoadducted oligonucleotide probes, (2) a method for the site-specific placement of a crosslinking site and/or a cross linking reagent during the enzymatic amplification of one or more segments of one or more nucleic acid targets, and (3) a hybridization method for discriminating between two or more nucleic acid base sequences in one or more nucleic acid targets that differ by a single base.

2. Description of the Prior Art

The ability of two polymers of nucleic acid containing complementary sequences to find each other and anneal through base pairing interactions is a well-recognized phenomenon. The initial observations of the "hybridization" process by Marmur and Lane, Proc. Nat. Acad. Sci., U.S.A. 46, 453 (1960) and Doty et al., Proc. Nat. Acad. Sci., U.S.A. 46, 461 (1960) have been followed by the refinement of this process into an essential tool of modern biology.

Initial hybridization studies, such as those performed by Hayashi et al., Proc. Nat. Acad. Sci., U.S.A. 50, 664 (1963), were performed in solution. Further development led to the immobilization of the target DNA or RNA on solid supports. With the discovery of specific restriction endonucleases by Smith and Wilcox, J. Mol. Biol. 51, 379 (1970), it became possible to isolate discrete fragments of DNA. Utilization of immobilization techniques, such as those described by Southern, J. Mol. Biol. 98, 503 (1975), in combination with restriction enzymes, has allowed for the identification by hybridization of single copy genes among a mass of fractionated, genomic DNA.

In spite of the progress made in methodology, a number of problems have prevented the wide scale use of hybridization as a tool in human diagnostics. Among the more formidable problems are a) the inefficiency of hybridization, b) the low concentration of specific target sequences in a mixture of genomic DNA, and c) the hybridization of only partially complementary probes and targets.

a. Inefficient Hybridization

It is experimentally observed that only a fraction of the possible number of probe-target complexes are formed in a hybridization reaction. This is particularly true with short oligonucleotide probes (less than 100 bases in length). There are three fundamental causes: 1) hybridization cannot occur because of secondary and tertiary structure interactions, 2) strands of DNA containing the target sequence have rehybridized (reannealed) to their complementary strand, and 3) some target molecules are prevented from hybridization when they are used in hybridization formats that immobilize the target nucleic acids to a solid surface.

Even where the sequence of a probe is completely complementary to the sequence of the target, i.e. the target's primary structure, the target sequence must be made accessible to the probe via rearrangements of higher-order structure. These higher-order structural rearrangements may concern either the secondary structure or tertiary structure of the molecule. Secondary structure is determined by intramolecular bonding. In the case of DNA or RNA targets this consists of hybridization within a single, contiguous strand of bases (as opposed to hybridization between two different strands). Depending on the extent and position of intramolecular bonding, the probe can be displaced from the target sequence, preventing hybridization.

Solution hybridization of oligonucleotide probes to denatured double-stranded DNA is further complicated by the fact that the longer complementary target strands can renature or reanneal. Again, hybridized probe is displaced by this process. This results in a low yield of hybridization (low "coverage") relative to the starting concentrations of probe and target.

The immobilization of target nucleic acids to solid surfaces such as nylon or nitrocellulose is a common practice in molecular biology. Immobilization formats eliminate the reassociation problem that can occur between complementary strands of target molecules, but not the problems associated with secondary structure effects. However, these mixed phase formats (i.e., Southern hybridization or dot blot hybridization) require time consuming fixation procedures. The hybridization reaction itself is kinetically much slower than a solution phase hybridization reaction. Together, the fixation and hybridization procedures require a minimum of several hours to several days to perform. Additionally, the standard immobilization procedures are often inefficient and result in the attachment of many of the target molecules to multiple positions on the solid surface, rendering them incapable of subsequent hybridization to probe molecules. Overall, these combined effects result in just a few percent of the initial target molecules being bound by probes in a hybridization reaction.

Yabusaki et al., U.S. Pat. No. 4,559,303, describe a nucleic acid hybridization assay employing probes that can be covalently crosslinked to their targets. A crosslinking reagent is required as well as a crosslinking site in both the probe and target nucleic acid sequences. The presence of the crosslinking reagent on the probe, by itself, does not effect the kinetics of hybridization, the specificity of base pairing, or the stability of the probe-target complex. Covalently crosslinked probes do have, however, several unique advantages over conventional probes, the most important of which is the ability to use denaturing conditions to remove non-specifically bound probe. This capability allows for simpler hybridization formats and permits the use of crosslinkable probes at concentrations much higher than conventional probes. This minimizes the impact of target strand reannealing. Another important advantage is the fact that crosslinkable probes can be covalently fixed to their targets at or above the melting temperature of the probe-target complex. This minimizes secondary structure interactions and maximizes rates. Provided certain criteria are met, hybridization and crosslinking can be carried out concurrently within a matter of minutes.

b. Low Target Sequence Concentration

In laboratory experiments, purified probes and targets are used. The concentrations of these probes and targets, moreover, can be adjusted according to the sensitivity required. By contrast, the goal in the application of hybridization to medical diagnostics is the detection of a target sequence from a mixture of genomic DNA. Usually the DNA fragment containing the target sequence is in relatively low abundance in genomic DNA. This presents great technical difficulties; most conventional methods that use oligonucleotide probes lack the sensitivity necessary to detect hybridization at such low levels.

One attempt at a solution to the target sequence concentration problem is the amplification of the detection signal. Most often this entails placing one or more labels on an oligonucleotide probe. In the case of non-radioactive labels, even the highest affinity reagents have been found to be unsuitable for the detection of single copy genes in genomic DNA with oligonucleotide probes. See Wallace et al., Biochimie 67, 755 (1985). In the case of radioactive oligonucleotide probes, only extremely high specific activities are found to show satisfactory results. See Studencki and Wallace, DNA 3, 7 (1984) and Studencki et al., Human Genetics 37, 42 (1985).

An alternate approach to the problem is to directly increase the concentration of the target prior to hybridization. Mullis et al., U.S. Pat. Nos. 4,683,195 and 4,683,202, describe a method for increasing the concentration of a segment of target sequence in a mixture of genomic DNA without cloning or purification. This process for amplifying the target sequence consists of introducing a molar excess of two oligonucleotide primers to the DNA mixture containing the desired target sequence. The two primers are complementary to their respective strands of the double-stranded target sequence. The mixture is denatured and then allowed to hybridize. Following hybridization, the primers are extended with a polymerase so as to form complementary strands. The steps of denaturation, hybridization, and polymerase extension can be repeated as often as needed to obtain a relatively high concentration of a segment of the desired target sequence. The length of the segment of the desired target sequence is determined by the relative positions of the primers with respect to each other, and therefore, this length is a controllable parameter. By virtue of the repeating aspect of the process, the method is referred to by the inventors as the "Polymerase Chain Reaction" (hereinafter PCR). Because the desired segments of the target sequence become the dominant sequences (in terms of concentration) in the mixture, they are said to be "PCR-amplified".

c. Partial Complementarity

Hybridization, regardless of the method used, requires some degree of complementarity between the sequence being assayed (the target sequence) and the fragment of DNA used to perform the test (the probe). (Of course, one can obtain binding without any complementarity but this binding is nonspecific and to be avoided.) For many diagnostic applications, it is not important to determine whether the hybridization represents complete or partial complementarity. For example, where it is desired to detect simply the presence or absence of pathogen DNA (such as from a virus, bacterium, fungi, mycoplasma, protozoan) it is only important that the hybridization method ensures hybridization when the relevant sequence is present; conditions can be selected where both partially complementary probes and completely complementary probes will hybridize. Other diagnostic applications, however, may require that the method of hybridization distinguish between variant target sequences. For example, it may be of interest that a particular allelic variant of a pathogen is present. These normal and variant sequences may differ in one or more bases.

There are other applications that may require that the hybridization method distinguish between partial and complete complementarity. It may be of interest to detect genetic polymorphisms. Human hemoglobin is composed, in part, of four polypeptide chains. Two of these chains are identical chains of 141 amino acids (alpha chains) and two of these chains are identical chains of 146 amino acids (beta chains). The gene encoding the beta chain is known to exhibit polymorphism. The normal allele encodes a beta chain having glutamic acid at the sixth position. The mutant allele encodes a beta chain having valine at the sixth position. This difference in amino acids has a profound (most profound when the individual is homozygous for the mutant allele) physiological impact known clinically as sickle cell anemia. It is well known that the genetic basis of the amino acid change involves a single base difference between the normal allele DNA sequence and the mutant allele DNA sequence.

Unless combined with other techniques (such as restriction enzyme analysis), hybridization methods that allow for the same level of hybridization in the case of both partial as well as complete complementarity are unsuited for such applications; the probe will hybridize to both the normal and variant target sequence.

Methods have been devised to enable discrimination between partial and complete complementarity. One approach is to take advantage of the temperature requirements of the specific hybridization under study. In typical melting curve experiments, such as those described by Wallace et al., Nucl. Acids Res. 6, 3543 (1979) and Nucl. Acids Res. 9, 879 (1981), an immobilized probe-target complex is washed at increasing temperatures under non-equilibrium conditions. It is observed that partially complementary probe-target complexes display a lower thermal stability as compared to completely complementary probe-target complexes. This difference can be used, therefore, to determine whether the probe has hybridized to the partially complementary or the completely complementary target sequence.

Conventional methods that utilize the temperature dependant nature of hybridization are artful. The application of this method for the discrimination of single base mutations in human genomic targets is limited to the use of short oligonucleotide probes where the hybridization interaction with the target sequence is in the size range of 17 bases to 25 bases in length. The lower length limit is determined by the random probability of having a complement to the probe in the human genome, which is greater than 1 for a random 16 base pair interaction, but less than 1 for interactions 17 bases or longer in length. The upper limit is one of practicality. It is difficult to differentiate single base mismatches on the basis of thermal stability for interactions longer than 25 bases in length. These conventional methods are, unfortunately, also time consuming. Probe concentrations in these experiments are approximately $1-5\times10^{-10}$M. These concentrations are empirically derived; they minimize the use of probe and simultaneously provide sufficient discrimination to distinguish single copy genes utilizing probes of approximately 20 nucleotides in length. Hybridization times are two to ten hours at these concentrations. After hybridization, several washes of varying stringency are employed to remove excess probe, non-specifically bound probe, and probe bound to partially complementary sequences in the target genome. Careful control of these wash steps is necessary, since the signal (specifically bound probe) to noise (non-specifically bound probe) ratio of the experiment is ultimately determined by the wash procedures.

No hybridization method heretofore described has solved all three of the problems discussed above. Crosslinkable oligonucleotide probes, while minimizing the factors of secondary structure, target strand reannealing, and partial complementarily, have not solved the problems of low target concentration. Furthermore, crosslinkable probes must be used in conjunction with targets that have a crosslink side. The PCR process by itself solves the problem of low target concentration. However, the specific detection of PCR products by any hybridization method is subject to the same problems associated with the detection of any target molecules. The detection of single base differences between PCR targets was initially accomplished through the use of a restriction enzyme analysis of the hybridization complexes formed between oligonucleotide probes and PCR targets. More recent studies have achieved discrimination without restriction enzymes, however these studies have involved the immobilization of target nucleic acids to solid surfaces (dot blot hybridization). Saiki et al., Nature 324, 163 (1986). As described in this application, the PCR process does provide a means of creating a specific crosslinking site in amplified target molecules. This is obviously necessary for targets that naturally lack a crosslinking site. It is also very important for targets (such as HIV-I) which naturally undergo rapid mutation in the course of their replication. Such targets have the potential being diagnosed as absent in a clinical specimen if the crosslinking site is lost by mutation.

One object of the present invention is to provide a method of hybridization that solves all three above-named problems.

Another object of the present invention is to provide a method of hybridization to detect the presence or absence of a pathogen or a specific genomic sequence in a clinical sample.

Another object of the present invention is to provide a method of hybridization to detect the presence or absence of a specific allelic variant of a pathogen or a specific allelic variant of a genomic sequence in a clinical sample.

Still another object of the present invention is to provide a method of hybridization to determine the genetic predisposition to a genetic disease by identifying specific allelic variants, in clinical samples, of nucleic acid which are genetically linked to the phenotypic expression of the disease.

A further object of the present invention is to provide a method of hybridization to determine genetic pedigree by identifying multiply-linked allelic variants of gene markers.

SUMMARY OF THE INVENTION

The present invention relates to a hybridization method for discriminating between complementarity and partial complementarity of DNA base sequences. The method is suitable for medical diagnostic purposes in that it overcomes the problems of low target concentration and hybridization inefficiency. Kinetic covalent entrapment of PCR-amplified target DNA is described through the use of crosslinkable probes. Problems with renaturation of target DNA in the hybridization reaction are minimized. Increased target coverage is obtained by cycling the hybridization steps thereby pumping the equilibrium between a probe and its target sequence.

Discrimination is shown between completely complementary probe-target sequences and probe-target sequences that differ in a single mismatch. This discrimination is achieved without the above-named disadvantages of conventional allele specific hybridization, providing a practical allele specific hybridization assay for diagnostic use.

DESCRIPTION OF THE DRAWINGS

FIG. 1 shows the primary structure of probes and targets used in the 04 human hemoglobin system.

FIG. 2 shows the primary structure of probes and targets used in the 08 human hemoglobin system.

FIG. 7 quantitates shows the discrimination of partial complementarity and complete complementarity of DNA base sequences as a function of the position of the mismatch relative to the crosslinking site.

FIG. 8; Panels A, B, and C; shows the enhanced discrimination achieved with a suppressor/competitor oligonucleotide in solution hybridization by polyacrylamide gel electrophoresis.

DESCRIPTION OF THE INVENTION

Figure 3:
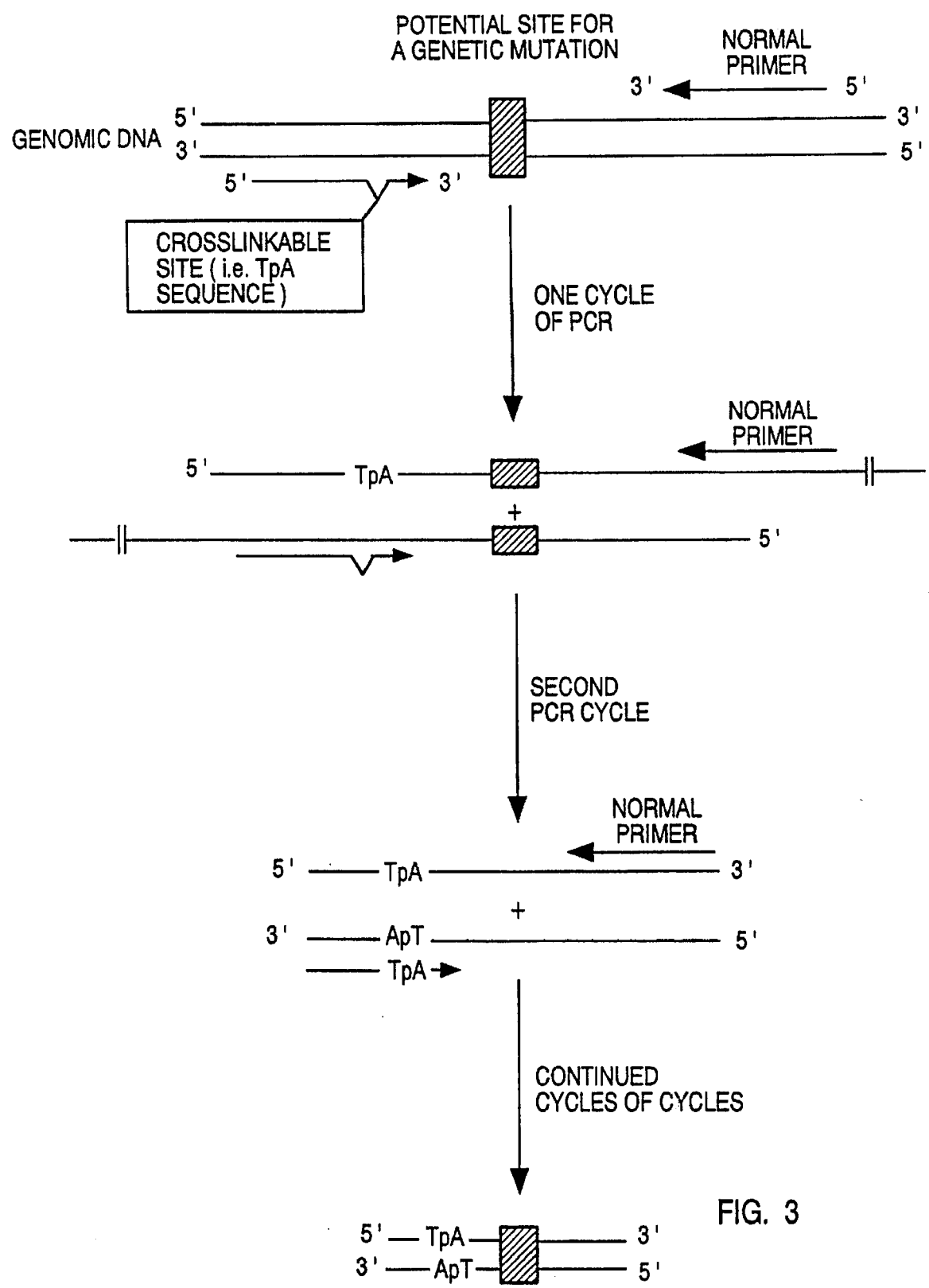
FIG. 3 shows diagrammatically the method by which a crosslinking site (i.e. TpA) is introduced into a PCR product from a target genome that lacks the crosslinking site.

This invention is a means for distinguishing between two target nucleic acid sequences (either DNA or RNA) that differ by one or more bases. In one medical diagnostic application, this invention is a means for differentiating between a heterozygotic and homozygotic target and, in the latter case, specifying which homozygote is present. Where a given genetic locus might code for allele A or allele a, the assay allows for the differentiation of an AA from an Aa from an aa pair of alleles. In another medical diagnostic application, this invention is a means for detecting the presence or absence of pathogens, as well as the presence or absence of specific allelic variants of pathogens, in clinical samples.

In the present invention, as with conventional hybridization techniques, discrimination of complete or partial complementarity is a function of temperature. The temperature dependant discrimination achieved via hybridization with crosslinkable probes was expected to be comparable with conventional hybridization. As noted above, the presence of the crosslinking reagent on the probe does not effect the specificity of the base pairing. The stability of the probe-target complex, furthermore, is not effected until the crosslinking step which takes place after base pairing. The only expectation of unambiguously identifying an allelic variation due to a point mutation was through the destruction of a crosslinking site. Nonetheless, the invention yields results that allow discrimination where the crosslinking site is adjacent to the site of sequence variation.

PCR-amplified targets are used. As noted above, the PCR process does not overcome the problem of reannealing of target strands during the hybridization step. In addition, the efficiency of the PCR process itself (i.e. the target production step) is hampered by reannealing. Crosslinkable probes are applied in conjunction with the PCR process such that reannealing is obviated in both of these steps.

a. Synthesis of the Probe

A photochemical synthesis of oligonucleotide probes containing site-specific psoralen monoadducts has been previously described by Gamper et al., Photochem. Photobio. 40:29 (1984). The present invention described an improved direct chemical method for the preparation of monoadducted probes using a modification of standard phosphoramidite chemistry.

The requisite furan side cis-syn 8-MOP:thymidine monoadduct was prepared and converted to its 5'-dimethoxytrityl-3'-β-cyanoethoxydiisopropylaminophosphoramidite derivative basically as described by Yabusaki et al., U.S. Pat. No. 4,599,303. The yield of 5'-DMT 8-MOP:thymidine monoadduct phosphoramidite, based on starting 8-MOP:thymidine monoadduct, was approximately 50%.

DNA synthesis was conducted in a step-wise automated method on a prototype Model 510 DNA synthesizer (Perkin-Elmer Cetus Instruments). The solid support used was a long-chain alkylamine controlled pore glass (CPG) functionalized with the 3'-terminal nucleoside derivative (American Bionetics, Hayward, Calif.). Because of the liability of the 8-MOP:thymidine moiety to strong aqueous base, it was necessary to make modifications to the standard synthesis protocol. The exocyclic amino groups of deoxyadenosine, deoxycytidine and deoxyguanosine were protected by 9-fluorenylmethoxycarbonyl (FMOC) groups as described by Webb et al., Nuc. Acids Res. 14, 7661 (1986), and Heikkila et al., Acta Chem. Scand. B37, 263 (1983). The FMOC protected nucleosides were 5'-dimethoxytritylated and converted to the corresponding 3'-β-cyanoethyl-N,N-diisopropyl (CED) phosphoramidites by standard procedures as described by Beaucage et al., Tetrahedron Letters 22, 1859 (1981). Thymidine CED phosphoramidite was obtained from American Bionetics. The amidites were used at an approximately thirty-fold molar excess (except the monoadduct phosphoramidite, which was used at approximately fifty-fold molar excess) and activated prior to coupling by "Activator Gold" (Beckman Instruments, Palo Alto, Calif.).

The synthetic cycle consisted of detritylation (3% v/v dichloracetic acid in dichloromethane), anhydrous acetonitrile wash, coupling (in the dark in the case of the psoralen containing amidite), anhydrous acetonitrile wash, capping [1:1 mixture of A) 20% v/v 2,6-lutidine, 20% v/v distilled N-methylimidazole in dry THF, and B) 10% v/v acetic anhydride in THF], oxidation (0.5% w/v iodine, 1% v/v 2,6-lutidine, 10% v/v water in THF), and acetonitrile wash.

Following the completion of the synthesis, the CPG was detritylated and washed and the support from each synthesis (ca. 20 mg) was dried in the dark and suspended in 1 ml of 1M 1,8-diazabicyclo[5.4.0]undec-7-ene (DBU) in acetonitrile for 15 minutes. This removed the FMOC and cyanoethyl protecting groups. The CPG washed with acetonitrile (3×1 ml) and suspended in concentrated aqueous ammonia for thirty minutes. This removed the deprotected oligomer from the CPG. The ammoniacal solutions were passed over NAP-10 columns (Pharmacia, Uppsalla, Sweden) which had been preequilibrated with water. The eluants from the NAP-10 columns were taken to dryness in the dark on the SpeedVac.

Examples of two sequences prepared by the chemical synthesis procedure are HRI-69 and HRI-70, which have the following sequences:

5'-*TAG TAA GAA TGT HRI-69

5'- AAA*TAG TAA GAA TGT HRI-70

3'- TTT AGC ATT CTT ACA HRI-68

As shown, HRI-70 is a three base extension of HRI-69. These sequences were selected to demonstrate the ability of an oligonucleotide containing a monoadduct at the 5' end to form crosslink and to show the monoadduct moiety was stable to additional synthetic cycles (i.e., DMT deprotection and oxidation steps). Following synthesis, HRI-69 and HRI-70 were characterized as follows. 5' end labelled (32P) HRI-68 (which is complementary to both HRI-69 and HRI-70) at $10^{-8}$M was mixed with different concentrations of either monoadducted oligonucleotide ($10^{-8}$ to $10^{-5}$M) under hybridization conditions then irradiated at 320–400 nm for 5 minutes. The samples were analyzed on a denaturing polyacrylamide gel followed by autoradiography. The autoradiogram showed the formation of crosslinks between HRI-69:HRI-68 and HRI-70: HRI-68. This result confirmed that the monoadduct phosphoramidite had been incorporated during the synthesis and some fraction of the monoadduct remained structurally intact during the subsequent synthetic steps. Second, each monoadducted oligonucleotide was 3' end labelled with cordycepin and terminal transferase then analyzed on a denaturing polyacrylamide gel. The autoradiogram showed two predominant bands for both HRI-69 and HRI-70 which corresponded to truncated 11-mer plus 12-mer monoadduct (HRI-69) and truncated 11-mer plus 15-mer monoadduct (HRI-70). The mobility of the bands with respect to the gel standards was as expected. To confirm the identity of the purported monoadduct bands, each was excised and eluted from the gel, mixed with 32P labelled HRI-68, then irradiated as described above. Each monoadduct band produced crosslink with HRI-68 as expected.

The chemical synthesis method offers several advantages over the photochemical procedure reported by Gamper et al. Photochmen. Photobio. 40: 29 (1984). First, it provides milligram instead of microgram amounts of product. Second, it does not depend on the fortuitous presence of a reactive 5' TpA site in the sequence of interest. Third, it provides a method to prepare long oligonucleotides with site specific monoadducts without a ligation step.

b. Production of Targets

The nucleic acid or acids used in the preparation of targets can be from any source, whether synthesized, cloned or naturally occurring, as long as they contain some part of the sequence of interest. In practice in a diagnostic assay, all targets are PCR amplified. In many of the specific examples given of this invention, PCR-amplified DNA fragments of naturally occurring human globin gene are used, as well as synthetic oligonucleotide targets containing sequences occurring in the human globin gene.

Crosslinkable probes can be used to block replication of a portion of one strand during the final stages of PCR. Such a procedure during the production of target step avoids the problems associated with strand reannealing during the hybridization. Because the concentration of the blocked strand is greatly exceeded by the concentration of the strand that is allowed to replicate, a large portion of the targets are unable to reanneal.

In some applications of present invention it is desirable to incorporate a crosslinking site in the PCR amplified target sequence. This can be performed with the PCR process when at least one of the primers carries a crosslinking site as a mutation with respect to the natural target sequence. For example, in the 04-MA system (FIG. 1), primer RS-118 brings in a crosslinking site into the PCR product which is not present in the genomic target DNA. In the 08-MA system (FIG. 2), the crosslinking site is created with primer HRI-12. In both FIGS. 1 and 2, base pairing schemes are indicated by the position of the oligonucleotides (primer, probes and oligonucleotide targets) above each other. The psoralen monoadduct is indicated by the stick figure adjacent to the T (T7). The difference between the 08 system and the 04 system is the position of the mismatch relative to the crosslinking site. In the 04 system, the mismatch is 8 bases on the 3' side of the psoralen monoadduct. In the 08 system, the mismatch is 5 bases on the 5' side of the psoralen monoadduct.

EXAMPLE 1

PCR amplification is used to incorporate a psoralen crosslinking site (i.e. 5'-TpA-3') into a segment of amplified nucleic acid (FIG. 3). One of the synthetically prepared oligonucleotide primers used in the PCR reaction is designed so that it carries a crosslinkable dinucleotide (i.e. a 5'-TpA-3' sequence) at a specific site. One or both of these bases are incorporated at the time of synthesis. They replace one or two natural bases in the normal primer sequence, and thus represent either a single or double mismatch when the primer is hybridized to its target sequence. The sequence of this primer and the crosslinking site can be chosen such that the crosslinking site can be incorporated at a desired distance away from a potential mutation site in a target sequence (i.e., adjacent to the sickle cell mutation site in the globin gene). This modified primer, along with the second normal primer, are hybridized to a target sequence. The sequence of the second primer determines the length of the amplified PCR products. Enzymatic extension and amplification are then carried out as usual. Upon completion of the amplification protocol, a crosslinkable site has been incorporated into the amplified segment of the target sequence at a specifically chosen site, and the PCR product is a specifically chosen length. This amplified segment of nucleic acid is then probed with an oligonucleotide containing a psoralen monoadduct at a position complementary to the synthetically incorporated crosslinkable site in the target sequence.

Figure 4A:
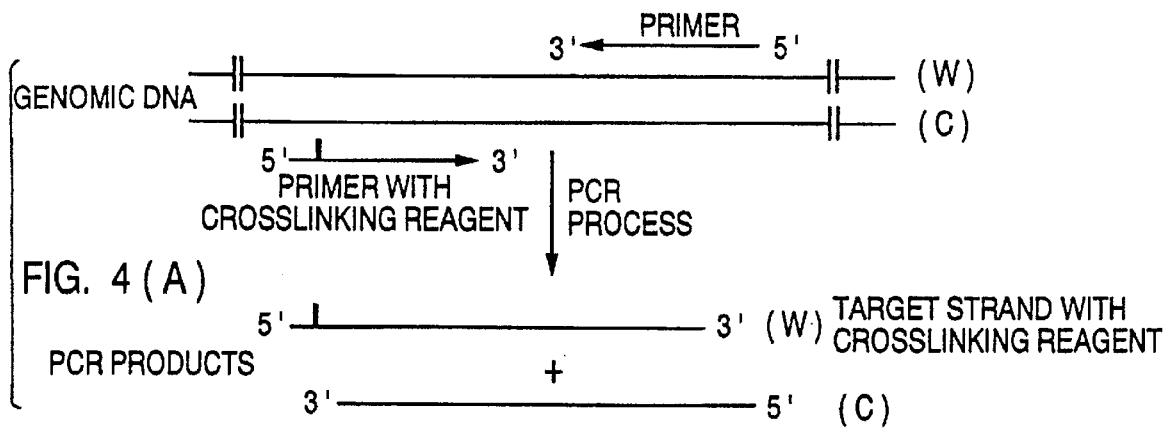
FIG. 4(A) shows diagrammatically one embodiment of the method by which a crosslinking reagent is introduced into a PCR product.
Figure 4B:
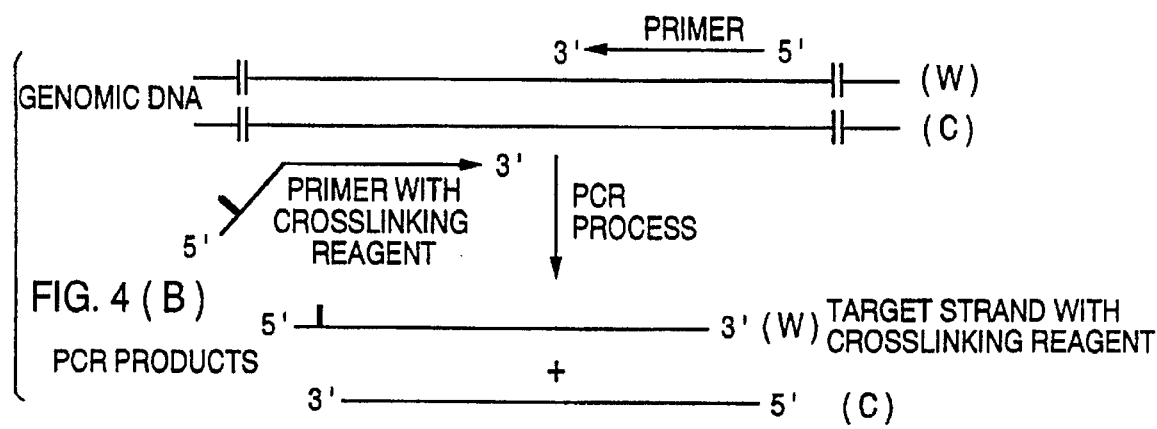
FIG. 4(B) shows diagrammatically another embodiment of the method by which a crosslinking reagent is introduced into a PCR product, wherein the crosslinking reagent is not in the region of the primer involved in hybridization.
Figure 4C:
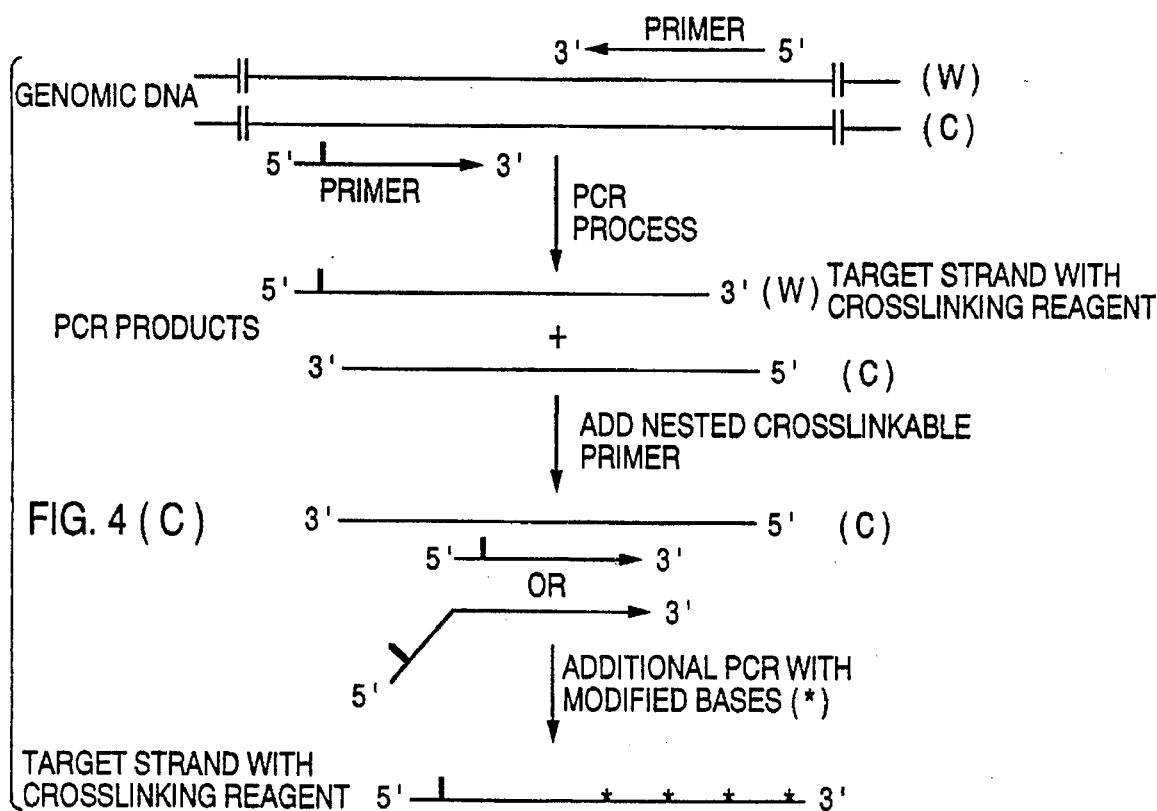
FIG. 4(C) shows diagrammatically another embodiment of the method by which a crosslinking reagent is introduced into a PCR product using a nested primer.

In other applications of the present invention it is desirable to incorporate a crosslinking reagent in the target DNA. This can also be done with the PCR process. A crosslinking reagent, such as a triphosphate of a psoralenthymine monoadduct may be incorporated enzymatically during the extension step of the PCR process. Alternatively, a site specific crosslinking reagent can be incorporated. One or both of the oligonucleotide primers can contain a crosslinking reagent. Extension of these primers by PCR will incorporate the crosslinking reagent into the longer target molecules (FIG. 4(A)). The crosslinking reagent need not necessarily be in a region of the primer required for hybridization (FIG. 4(B)). A variant of the above procedure is the use of a nested primer which is contained within the target sequence defined by the 3' ends of the original primers (FIG. 4(C)). Again, the nested primer can contain a crosslinking reagent within the segment of the nested primer that is involved in the hybridization reaction with the PCR amplified segment of the target molecule, or the crosslinking reagent can be positioned in a region of the nested primer that is not involved in the hybridization reaction with the PCR amplified segment of the target molecule. This nested primer can be extended during later cycles of the PCR process and in the presence of modified bases, such as biotin-UTP. These target molecules can then be covalently linked to conventional complementary probe molecules and subsequently detected by the presence of the modified base.

c. Hybridization Formats

Monoadducted oligonucleotide probes can be covalently fixed to PCR amplified targets, which will eliminate subsequent probe displacement which occurs when PCR strands reanneal in solution. Solving this problem is important for the development of a solution hybridization assay with double stranded target systems, and especially important for mixed phase assay systems in which the hybridization reaction is driven by high concentrations of PCR amplified targets.

EXAMPLE 2

Figure 5:
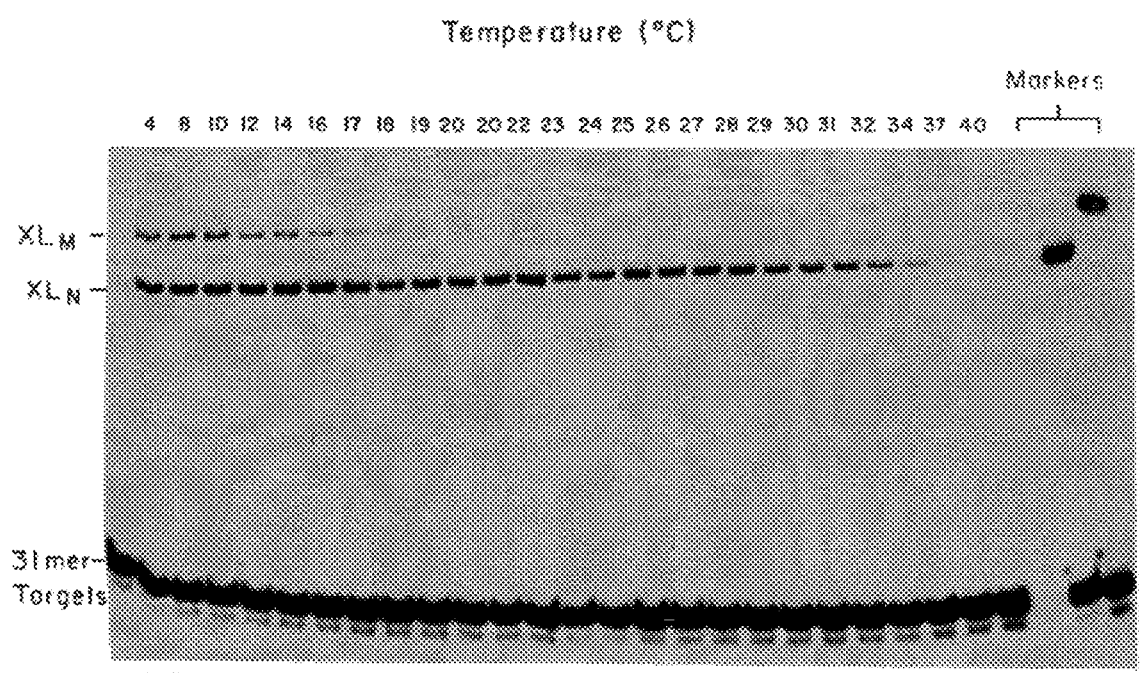
FIG. 5 shows the discrimination of partial complementarity and complete complementarity of DNA base sequences in solution hybridization by polyacrylamide gel electrophoresis.

Unexpected results were obtained from solution hybridization experiments utilizing a crosslinkable probe with two radiolabelled oligonucleotide targets: 1) a completely complementary target (normal target), and 2) a target with a DNA sequence that differed only in a single base (mutant target). The sequences of the two 31-mer targets are subsets of the 135 base pair PCR fragments, which were generated from genomic DNA that was extracted from Mut-4 and SC-1 cells, and which represent the normal and sickle cell mutation sequences respectively. The probe used was a monoadducted 16-mer of the 08 system. The monoadducted probe was at a concentration that allowed hybridization to reach equilibrium in a few seconds. The hybridization buffer consisted of 0.01M Tris (pH=7.0), 1 mM EDTA, 30% formamide, and 3.0M tetramethylammonium chloride. A chaotropic salt was used to minimize sequence specific effects on the hybridization interactions. The targets were denatured, placed at the hybridization temperature, and irradiated at this temperature. Many hybridization temperatures were used between 4° and 40° C. (the products at each temperature are shown in each gel lane). The products of the hybridization were isolated by precipitation and centrifugation and then electrophoresised on a denaturing polyacrylamide gel which was analyzed by autoradiography. The results are shown in FIG. 5. The free (uncomplexed) $^{32}$P-labelled, 31-mer targets run to the bottom of the gel. The probe:mutant target complex ($XL_m$) is retarded in the gel, running above the probe:normal target complex ($XL_n$). It is clear that the melting temperature for the mutant target was 12° C. lower than the melting temperature of the normal target.

It is not yet known whether this large melting temperature difference represents an enhancement brought about by the presence of the crosslinking reagent. It may be due to the fact that hybridization (and crosslinkage) under these conditions occurs at equilibrium in contrast to conventional hybridization, where discrimination occurs under non-equilibrium conditions. At equilibrium and above the melting temperature of the probe:mutant target complex, there is a strong preference for the probe to bind preferentially to the normal target. This preference may depend upon the position of the crosslinking site in the probe:target complex. Indeed, it may be possible to enhance discrimination between normal and mutant target sequences by positioning the crosslinking site at a precise position relative to the mismatch site of the probe:target complex. This can be accomplished through the use of specifically chosen PCR primers.

FIG. 5 also demonstrates that covalent probe:target complexes of identical molecular weight can be resolved by standard polyacrylamide gel electrophoresis (PAGE) when one of the complexes contains at least a single base mismatch between the target and the probe. This resolution requires that both the normal and mutant target oligonucleotides be of identical length, and that the crosslinking site be precisely positioned relative to the mismatch site in the probe target complex. Again this is accomplished through the use of specifically chosen PCR primers.

EXAMPLE 3

Figure 6A:
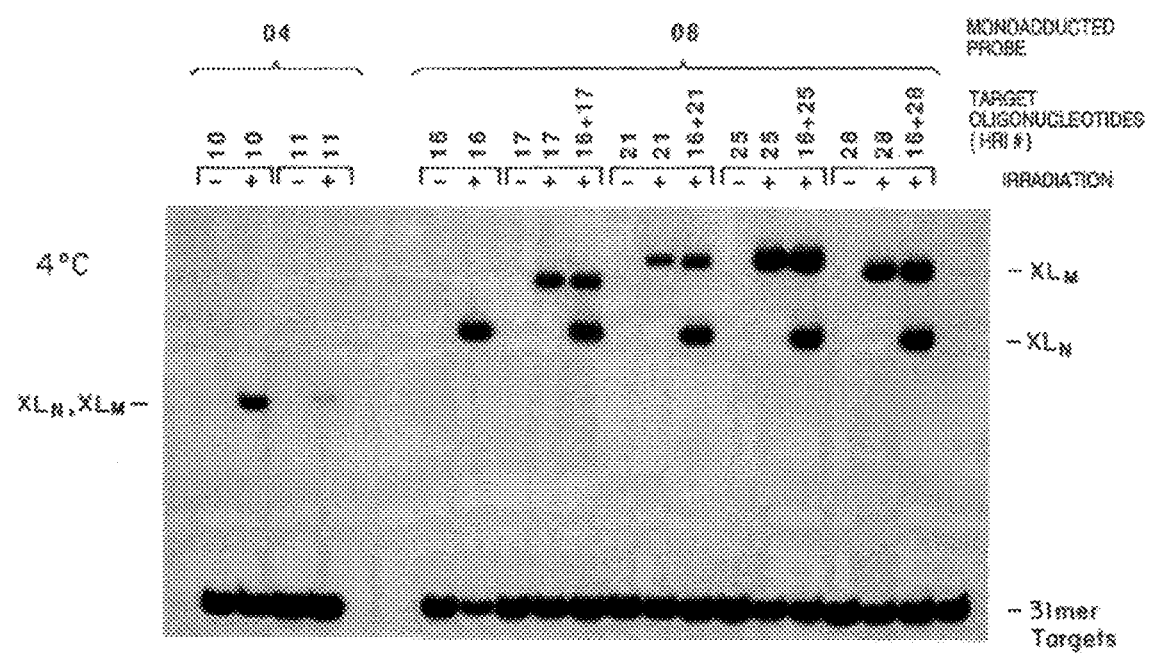
FIG. 6(A) shows the discrimination at 4° C. of partial complementarity and complete complementarity of DNA base sequences as a function of the position of the mismatch relative to the crosslinking site in solution hybridization by polyacrylamide gel electrophoresis.
Figure 6B:
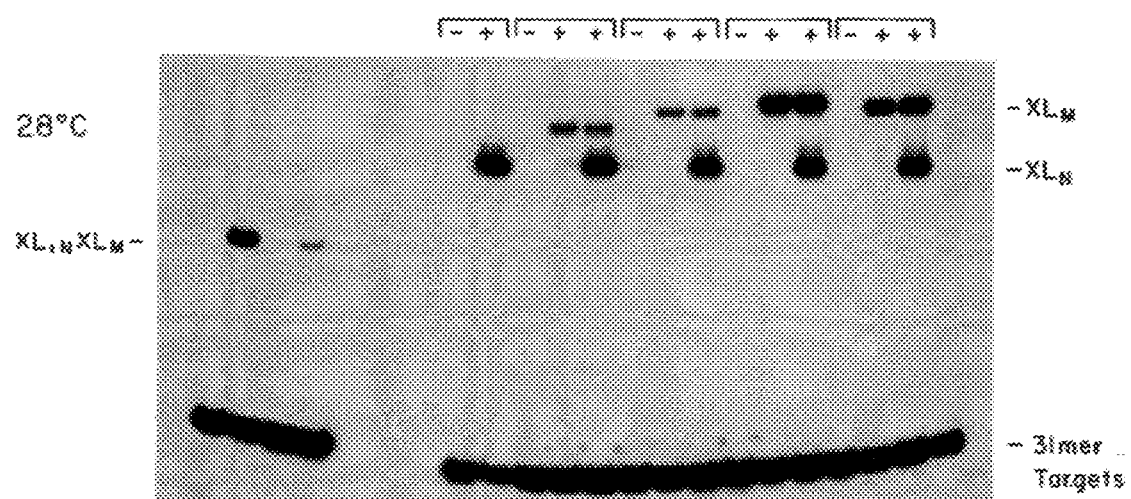
FIG. 6(B) shows the discrimination at 28° C. of partial complementarity and complete complementarity of DNA base sequences as a function of the position of the mismatch relative to the crosslinking site in solution hybridization by polyacrylamide gel electrophoresis.
Figure 6:
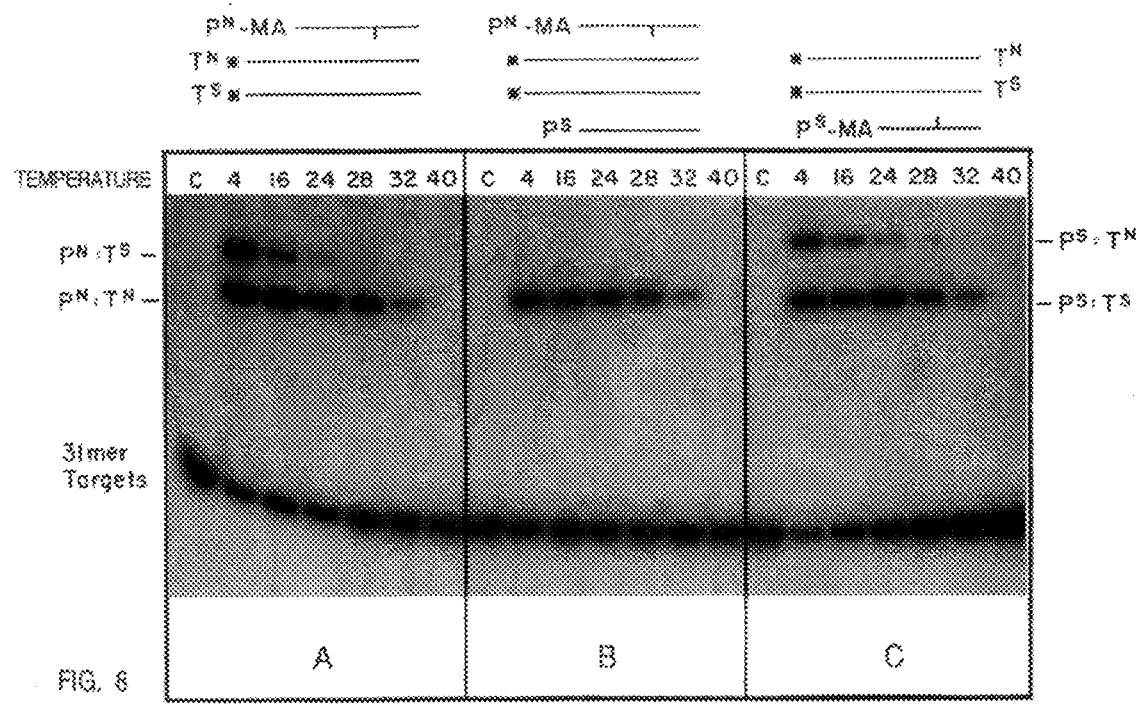

FIGS. 6 and 7 illustrate the best mode of carrying out the invention. Discrimination is measured as a function of the position of the mismatch relative to the crosslinking site. Both the 08 system and the 04 system were used. Target oligonucleotide sequences are referred to by the numbering system described previously (FIGS. 1 and 2). Discrimination was measured at either 4° C. or 27° C.—temperatures at which both hybridization and crosslinkage were conducted. Unirradiated samples were run as controls. The conditions were in other respects (buffer, isolation steps, gel electrophoresis, etc.) similar to those in Example 2. FIG. 6(A) and 6(B) show the autoradiogram of the gel products of the hybridization reaction conducted at either 4° C. or 27° C., respectively. It is to be noted that in both FIG. 6(A) and 6(B), the migration of 04 probe crosslinked to HRI-10 targets is the same as the migration of 04 probe crosslinked to HRI-11 targets. In other words, the probe:mutant(single base mismatch) target complex cannot be distinguished from the probe:normal target complex using the 04 probe. On the other hand, the probe:mutant target complex is distinguished from the probe:normal target complex (08-MA XL HRI-16) using the 08 probe.

The ability to resolve these products is the basis of discriminating between having a point mutation or containing normal DNA in the sequence region of interest. When either of these bands are present alone in a gel analysis of the probe:target crosslinked products, the individual in question would be considered homozygous for either the normal or the mutation, depending upon which band was present. When both bands are present, the individual would be considered a heterozygote.

For the purposes here, discrimination is defined as the ratio of a normal probe bound to a normal target relative to the normal probe bound to a mutant target under identical equilibrium conditions. Discrimination was measured with the 08-MA system. The bands from FIGS. 6(A) and 6(B) were simply excised and counted. The results are summarized in FIG. 7. In addition to the requirements of 1) a psoralen monoadducted probe, and 2) a target molecule of a short and precise length, FIG. 7 shows that the best discrimination is achieved when the mutation in question is orientated in a specific site relative to the crosslinking site.

For most types of gel analysis, discrimination (as strictly defined above) should be minimized, i.e. the amount of normal probe bound to a normal target and normal probe bound to a mutant target should be approximately equal. This allows for the simultaneous identification of each product with a single probe if both are present. For other types of analysis, it may be desirable to maximize discrimination, i.e. establish conditions where either the normal or the mutant are selectively captured.

EXAMPLE 4

Another method of practicing the invention involves attaching the probe to a solid support. Specifically, polystyrene beads with surface carboxylic acid groups were coupled to 4'-hydroxymethyl-4,5', 8-trimethylpsoralen monoadducted probe (a 16-mer, HRI-23, with an aminopolyether tail at the 5' end) using a water soluble carbodiimide. The method of attachment is described generally by Kremsky, J. et al., Nucleic Acids Research 15, 2891 (1987).

Target nucleic acids from MUT-4 cells (normal sequence) and SC-1 cells (sickle cell sequence) were prepared by PCR amplification using primer molecules RS-118 and KM-38. The two PCR product sequences differ by a single base. Following PCR, each fragment was isolated on an 8% denaturing polyacrylamide gel and labelled by kinasing.

Experimental points utilized 50 ul of a 3% bead solution which contained 38 fmol/ul of monoadducted probe. The final probe concentration was $4 \times 10^{-8}$M. Either MUT-4 or SC-1 PCR product was added to each sample tube at a concentration of approximately $2 \times 10^{-10}$M.

Each experimental sample (two per set) was irradiated five cycles. One cycle consists of a) denaturation carried out at 85° C. for 5 minutes, b) hybridization carried out at 30° C. temperature for 3 minutes and c) irradiation carried out at 30° C. for 5 minutes. The control samples (one per set) were identical to the experimental samples but were not irradiated. Following irradiation, the beads were washed (five times at 50° C. in 50mM $Na_2HPO_4$/0.05% SDS). At this point either 1) the captured targets were recovered by photoreversal of the crosslinking reaction, or 2) the beads were counted in scintillation fluid. In the latter case, bead recovery was determined by tritium counts while PCR fragment capture was determined by 32p. Under these conditions, discriminatory capture was 23:1 in favor of the normal sequence.

EXAMPLE 5

The bead experiment described in Example 4 was performed in the same manner except that the polyacrylamide gel isolation step was omitted. The beads containing probes were added directly to the PCR amplified targets.

EXAMPLE 6

The bead experiment described in Example 4 was performed in much the same manner except that the beads used were magnetic beads.

EXAMPLE 7

Another method of practicing the invention involves the use of RNA. DNA targets are made from RNA templates using reverse transcriptase. Murakawa et al., DNA 7, 287 (1988). Thereafter, the DNA targets are used in the amplification and hybridization steps in the same way as Examples 2, 4, 5 or 6.

EXAMPLE 8

Teflon was substituted as the solid support in EXAMPLE 4. A cleavable teflon support can be obtained from Molecular Biosystems, Inc. The oligonucleotide is attached to the support at its 3' end with a 25 atom spacer in between. The steps are then carried out in much the same way as in EXAMPLE 4.

EXAMPLE 9

In the experiments described in Examples 2 and 4–7, chemical crosslinking may be used instead of photochemical crosslinking. Webb et al. Nuc. Acids Res. 14, 7661 (1986).

EXAMPLE 10

In the experiments described in Examples 2 and 4–7, a combination of chemical crosslinking and photochemical crosslinking may be used.

EXAMPLE 11

In a situation where a single fragment of target DNA contains two or more sites of allelic variation, the fragment may be simultaneously probed with two allele specific crosslinkable probes. The products of such a hybridization may be examined by any of the methods used above. Given two sites with two sequence patterns at each site, the possible linkage patterns which will emerge are AB, aB, Ab, or ab. The power of such a procedure for clinical characterization and parental testing as the number of sites increases and the variation at individual sites increases is considerable.

The examples given above demonstrate that it is possible using the 08 system to quantitatively measure discrimination of a single mismatch in a hybridization assay with short crosslinkable probes. It is possible to further increase this discrimination through the addition of a "suppressor" oligonucleotide which is complementary to the target oligonucleotide that one desires not to capture. This approach is based on the empirical observation that normal probe (i.e. probe having the normal sequence) preferentially binds to normal targets and mutant probe (i.e. probe having the mutant sequence) preferentially binds to mutant target.

Specifically, a mutant probe lacking crosslinking reagents and a normal, monoadducted probe are introduced to the target preparation. Binding of the normal probe to mutant targets is blocked since these mutant target molecules have a thermodynamic preference for the mutant probes. This type of assay can be used with a bead (or membrane format) where the beads (or membrane) are coupled to a mixture of normal probes and mutant probes, only one of which contains a crosslinkable group. This type of assay can also be performed in a solution format and analyzed on gels as described below.

EXAMPLE 12

Discrimination is enhanced via a suppressor oligonucleotide. The synthetic oligonucleotides from the 08 system were used; HRI-08 and HRI-08-MA (normal probes), HRI-19 and HRI-19-MA (mutant probes), HRI-16 (a normal 31-mer target), and HRI-17 (a mutant 31-mer target). HRI-16 and HRI-17 were 32p labelled and purified by electrophoresis before use.

Samples were prepared in a chaotropic salt buffer (1× TE buffer, 30% formamide, 3.0M tetramethylammonium chloride) with a total volume of 10 ul. The labelled targets (both HRI-16 and HRI-17) were used at $1 \times 10^{-8}$M. Probe molecules (probes with and without crosslinking reagents) were used at $3.7 \times 10^{-8}$M. After preparing the samples, they were heat denature at 50° C. for 5 minutes. They were hybridized for 1 minute at the indicated temperatures, and then irradiated at this same temperature for 5 minutes. All the samples were ethanol precipitated and then analyzed on a 20% polyacrylamide, 7M urea gel.

FIG. 8 is an autoradiogram showing the crosslinked products as a function of hybridization and irradiation temperature. In panel A, only a monoadducted normal probe (08-MA) was present during the hybridization. This probe crosslinks to both the normal and the mutant targets, with a preference for the normal target. In panel C, only a monoadducted mutant probe (19-MA) was present during the reaction. Again this probe hybridizes to both its completely complementary sequence and the partially complementary sequence. In complete analogy with the 08-MA probe, the mutant probe (19-MA):normal target complex is retarded in the gel with respect to the position of the mutant probe crosslinked to the normal target.

In Panel B, a monoadducted normal probe (08-MA) was used in conjunction (1:1 ratio) with a mutant probe lacking crosslinking reagents. Very little of the 08-MA probe was observed to crosslink with the mutant target. The 08-MA probe, however crosslinked to the normal target to the same extent as it did in the absence of the suppressor oligonucleotide.

To quantify this effect, the crosslinked bands were excised and counted. The fraction of the targets hybridized and crosslinked was determined at each temperature, and from this data discrimination was determined (ratio of normal probe/normal target complexes to the normal probe/mutant target complexes). This data is plotted in FIG. 9.

Figure 9:
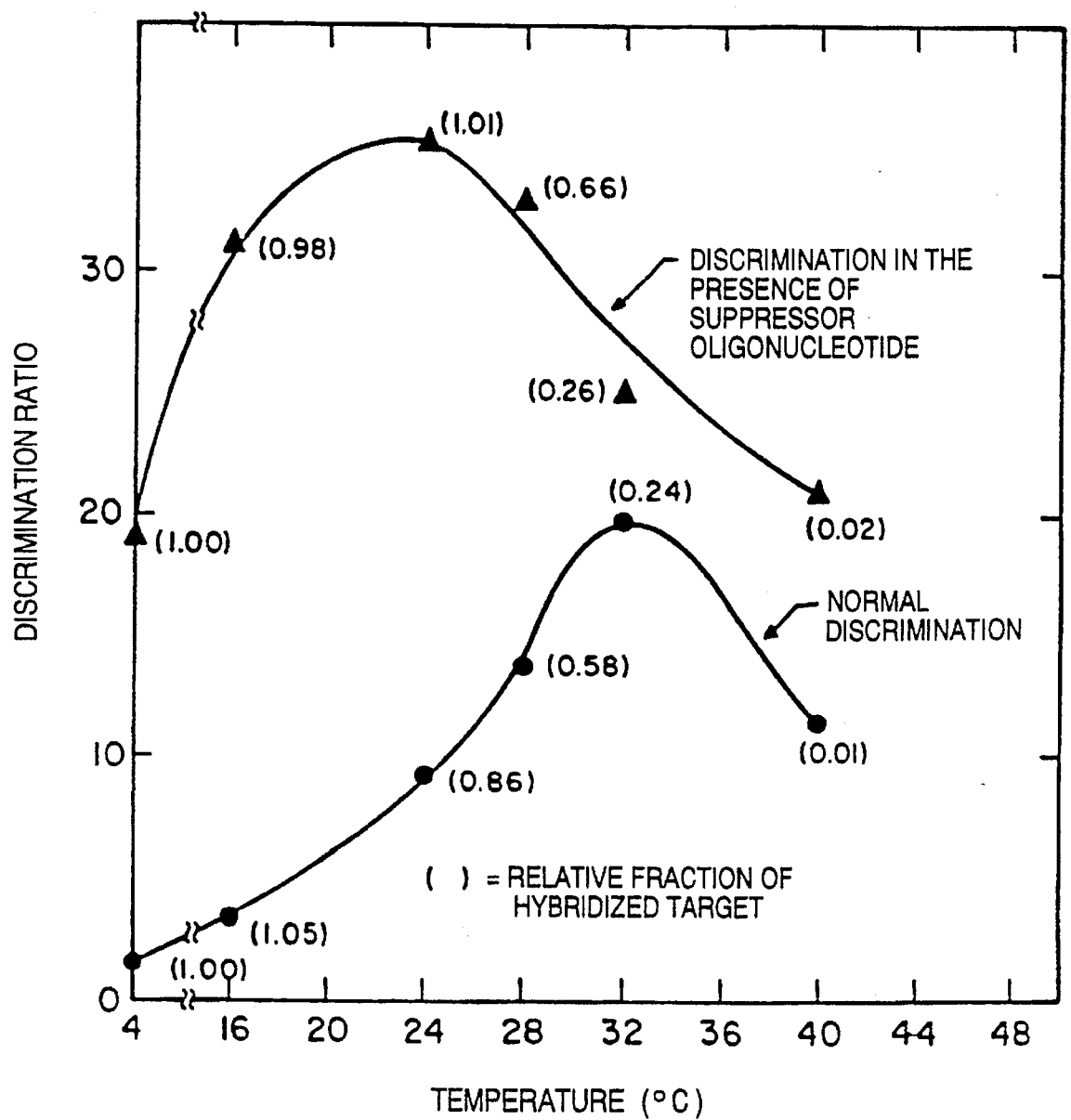
FIG. 9 quantifies the enhanced discrimination achieved with a suppressor/competitor oligonucleotide (FIG. 8).

FIG. 9 shows that the additional "suppressor" oligonucleotide enhances discrimination, particularly at temperatures below the melting temperature of the completely complementary complex (28° C.). The relative fraction of target molecules hybridized is also shown. With conventional equilibrium conditions, discrimination is sharply dependant upon temperature, with maximum discrimination occurring slightly above the melting temperature of the completely complementary probe target complex. At this temperature the relative fraction of target molecules hybridized is only about 25%. When the additional suppressor oligonucleotide is present, discrimination is relatively insensitive to hybridization temperatures between the melting temperature of the completely complementary probe target complex (28° C.) and the melting temperature of the partially complementary probe target complex (16° C.). Within this temperature region, the relative hybridization efficiency is constant and maximum (near 100%). Discrimination is also maximum in this region. This technique (equilibrium hybridization/crosslinking with a mixture of crosslinkable and non-crosslinkable probes), therefore, provides a relatively temperature insensitive procedure for identifying point mutations.

As noted earlier, it may be of interest to detect the presence or absence of pathogen DNA (such as from a virus, bacterium, fungi, mycoplasma, protozoan). It may also be of interest that a particular allelic variant of a pathogen is present. These normal and variant sequences may differ in one or more bases. The invention provides a method for such discrimination. At present, there is great interest in detecting Human Immunodeficiency Virus (HIV). Most methods now in clinical use measure HIV only indirectly; such methods are aimed at detecting host antibodies elicited in response to infection. Methods aimed at directly detecting HIV DNA are hampered by the presence of 1) an extremely high mutation rate associated with HIV, and 2) extremely low levels of viral DNA in clinical samples. The present invention overcomes these problems. Of particular importance to the former problem is the ability with the present invention to introduce crosslinking sites into the targets at specific sites during the amplification step. This ensures the existence of a crosslinking site in the sequence of a PCR amplified target. Of particular importance to the latter problem is the ability with the present invention to cycle the hybridization steps (denaturation/irradiation) thereby pumping the equilibrium to increase the coverage and, consequently, the signal.

EXAMPLE 13

Figure 10:
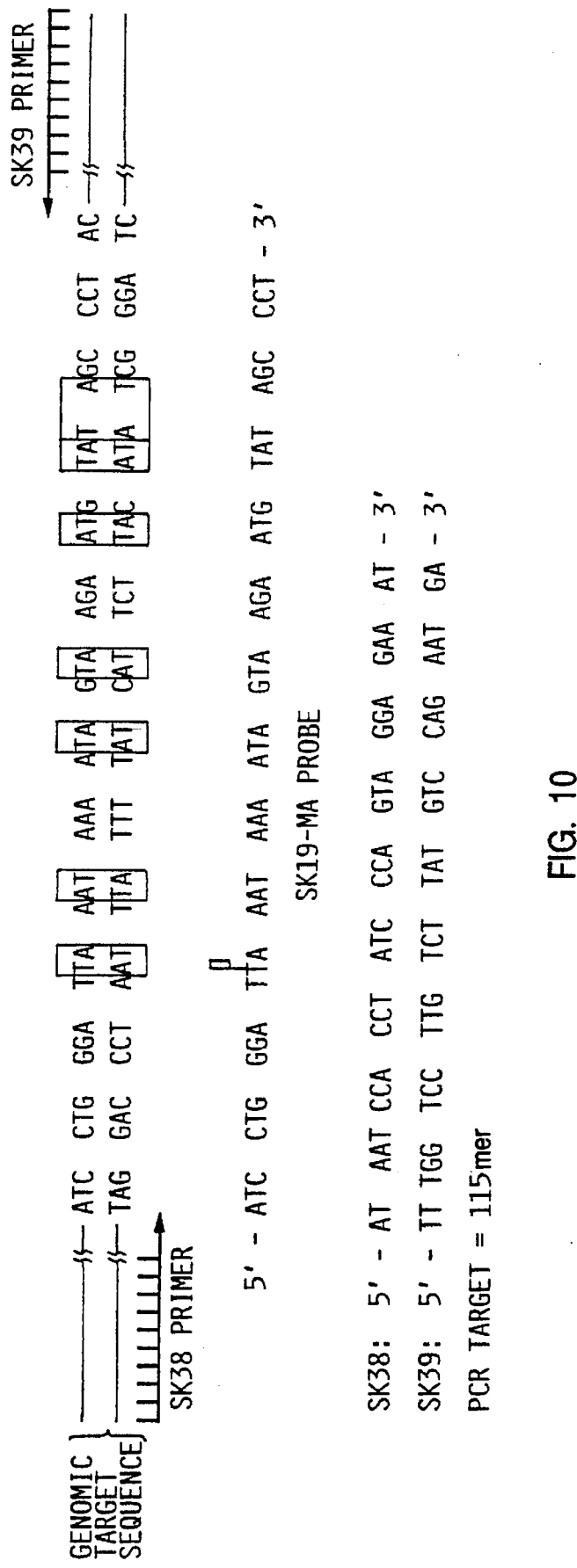
FIG. 10 shows the DNA oligonucleotide system for PCR amplification and subsequent detection of HIV DNA by hybridization.

DNA template was obtained from blood samples taken from human patients known to be positive for HIV-I. The DNA oligonucleotide system for PCR amplification and subsequent detection of HIV DNA by hybridization with SK-19 or SK-19-MA is shown in FIG. 10. The arrows indicate the polymerase extension direction for the primers. The HMT monoadduct on SK-19-MA is shown by (7). Blocks ☐ denote natural potential 5-TpA-3' crosslinking sites in the DNA sequence of HIV.

10 ul of template was amplified using primer pair SK-38/SK-39 for thirty cycles. Following amplification, 3.3 ul of monoadducted $^{32}$P labelled 41-mer probe was added (SK-19-MA) at a final concentration of $8 \times 10^{-9}$M. Following a 5 minute heat denaturation at 90°–95° C., samples were irradiated at 55° C. for 5 minutes. This denaturation/irradiation cycle was repeated two more times. For analysis, samples were heat denatured and then run on a denaturing (8M urea) 12% polyacrylamide gel.

As controls, the same experiment was done on an 1) amplified, unirradiated sample, 2) irradiated, unamplified sample, and 3) unirradiated, unamplified sample.

Figure 11:
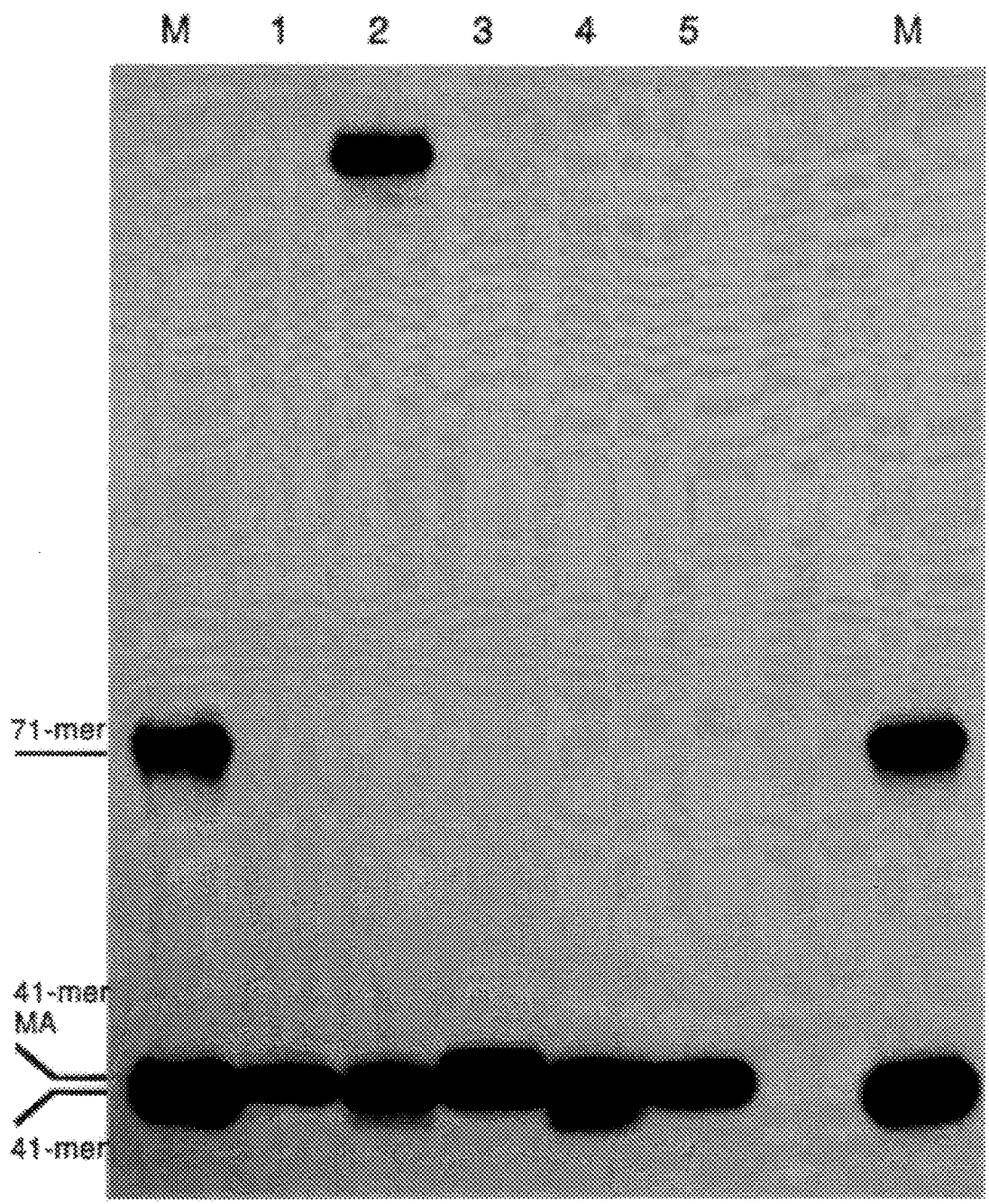
FIG. 11 shows the detection of HIV DNA from PCR amplified DNA of HIV-infected human cells by polyacrylamide gel electrophoresis.

FIG. 11 is an autoradiogram of the results. Lanes marked "M" are markers, showing unmodified 41-mer (SK-19) and 71-mer (the latter marker not pertinent here). Lane 1 is unirradiated 41-mer monoadducted probe (SK-19-MA) alone. Lane 2 is irradiated amplified sample plus probe. Lane 3 is unirradiated amplified sample plus probe. Lane 4 is irradiated unamplified sample plus probe. Lane 5 is unirradiated unamplified sample plus probe.

The autoradiograph shows 115-mer:41-mer crosslinked product in Lane 2 only. Thus, the generation of signal is shown to depend on both irradiation and amplification. Most importantly, the autoradiograph demonstrates the resolution on a denaturing polyacrylamide gel of free monoadducted probe (SK-19-MA) and the covalent complex between the monoadducted probe and the 115-mer generated by PCR amplification of DNA extracted from HIV-infected human cells.

I claim:

1. A method for discriminating between nucleic acid base sequences in two nucleic acid target molecules, comprising:
   a) providing, in any order, i) first and second nucleic acid target molecules that differ by at least one base in their nucleic acid base sequences, ii) a first single stranded nucleic acid probe which is characterized as having a complementary base sequence to said nucleic acid base sequence of said first nucleic acid target molecules, iii) a second single stranded nucleic acid probe, which is characterized as having a complementary base sequence to the nucleic acid base sequence of said second nucleic acid target molecules, and containing a covalently attached psoralen monoadduct capable of forming covalent bonds between said second single stranded nucleic acid probe and said second nucleic acid target molecules, and iv) a reaction containing means;
   b) adding, in any order, to said reaction containing means to create a reaction mixture, said first and second nucleic acid target molecules and said first and second single stranded nucleic acid probes, so as to create noncovalent, completely complementary and partially complementary probe:target complexes under conditions between the melting temperatures of the completely complementary complexes and the partially complementary complexes, allowing for the discriminatory hybridization of said single stranded nucleic acid probes to their respective nucleic acid target molecules;
   c) treating said reaction mixture such that said psoralen forms covalent bonds between said second single stranded nucleic acid probe molecules and said second nucleic acid target molecules so as to create covalent probe:target complexes; and
   d) subjecting said reaction mixture to a means for separating covalent probe:target complexes from uncrosslinked probe molecules and target molecules.

2. The method of claim 1 wherein said separation means consists of polyacrylamide gel electrophoresis.

3. The method of claim 1 further comprising, prior to the step of sub-part b, attaching said second single stranded nucleic acid probe to a solid support.

4. The method of claim 3 wherein said solid support consists of functionalized polystyrene having surface groups appropriate for activation and coupling.

5. The method of claim 1 wherein said covalent bonds are formed photochemically.

6. The method of claim 1 wherein said target molecules are labelled.

7. The method of claim 6 wherein said label is chosen from among radioactive labels, immunogenic labels, chromogenic labels, and fluorogenic labels.

8. A method for discriminating between nucleic acid base sequences in two nucleic acid target molecules that differ by a single base, comprising:
   a) providing, in any order, i) first and second nucleic acid target molecules that differ by a single base in their nucleic acid base sequences, ii) a first single stranded nucleic acid probe which is characterized as having a complementary base sequence to said nucleic acid base sequence of said first nucleic acid target molecules and capable, thereby, of hybridizing to said first nucleic acid target molecules to create completely complementary complexes having a melting temperature, iii) a second single stranded nucleic acid probe, which is characterized as having a complementary base sequence to the nucleic acid base sequence of said second nucleic acid target molecules, capable, thereby, of hybridizing to said second nucleic acid target molecules to create completely complementary complexes having a melting temperature, and containing a covalently attached psoralen monoadduct capable of forming covalent bonds between said second single stranded nucleic acid probe and said second nucleic acid target molecule, and iv) a reaction containing means;
   b) adding, in any order, to said reaction containing means to create a reaction mixture, said first and second nucleic acid target molecules and said first and second single stranded nucleic acid probes;
   c) subjecting said reaction mixture to temperatures below the melting temperatures of said completely complementary complexes, to allow for the discriminatory hybridization of said probes to their respective target molecules;
   d) treating said reaction mixture such that said psoralen forms covalent bonds between said second single stranded nucleic acid probe molecules and said second nucleic acid target molecules so as to create covalent probe:target complexes; and e) subjecting said reaction mixture to a means for separating covalent probe:target complexes from uncrosslinked probe molecules and target molecules.

9. The method of claim 8 wherein said separation means consists of polyacrylamide gel electrophoresis.

10. The method of claim 8 further comprising, prior to the step of sub-part b, attaching said second single stranded nucleic acid probe to a solid support.

11. The method of claim 10 wherein said solid support consists of functionalized polystyrene bead.

12. The method of claim 8 wherein said covalent bonds are formed photochemically.

13. The method of claim 8 wherein said target molecules are labelled.

14. The method of claim 13 wherein said label is chosen from among radioactive labels, immunogenic labels, chromogenic labels, and fluorogenic labels.

* * * * *